(12) United States Patent
Seck

(10) Patent No.: US 9,345,547 B2
(45) Date of Patent: May 24, 2016

(54) APPARATUS AND METHOD FOR SIZING A CONNECTING ELEMENT FOR POSITIONING ALONG A BONE STRUCTURE

(75) Inventor: Trevor Seck, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 146 days.

(21) Appl. No.: 13/088,941

(22) Filed: Apr. 18, 2011

(65) Prior Publication Data

US 2012/0265212 A1 Oct. 18, 2012

(51) Int. Cl.
*A61B 17/56* (2006.01)
*A61B 19/00* (2006.01)
*A61B 17/70* (2006.01)

(52) U.S. Cl.
CPC .............. *A61B 19/46* (2013.01); *A61B 17/708* (2013.01); *A61B 2019/461* (2013.01); *A61B 2019/467* (2013.01)

(58) Field of Classification Search
CPC ............. A61B 19/46; A61B 2019/467; A61B 2019/461; A61B 17/708
USPC ........... 606/86 R, 87, 90, 102, 104, 105, 86 A
See application file for complete search history.

(56) References Cited

U.S. PATENT DOCUMENTS

| | | | | |
|---|---|---|---|---|
| 2,045,298 | A * | 6/1936 | Hanle | B43L 9/02 33/27.02 |
| 4,226,025 | A * | 10/1980 | Wheeler | G01B 3/166 33/512 |
| 4,335,715 | A * | 6/1982 | Kirkley | A61B 17/15 606/329 |
| 6,648,891 | B2 * | 11/2003 | Kim | A61B 17/0206 606/102 |
| 7,275,336 | B2 * | 10/2007 | Casutt et al. | 33/797 |
| 7,618,424 | B2 * | 11/2009 | Wilcox | A61B 17/025 606/105 |
| D638,322 | S * | 5/2011 | Teramoto | D10/73 |
| 8,192,440 | B2 * | 6/2012 | Jones | A61B 17/7091 606/86 A |
| 2004/0176779 | A1 * | 9/2004 | Casutt | A61B 17/1757 606/102 |
| 2004/0267279 | A1 * | 12/2004 | Casutt | A61B 19/46 606/104 |
| 2005/0203532 | A1 * | 9/2005 | Ferguson | A61B 17/025 606/90 |
| 2007/0173745 | A1 * | 7/2007 | Diederich | A61B 5/107 600/587 |
| 2008/0039841 | A1 * | 2/2008 | Casutt | A61B 19/46 606/86 A |
| 2008/0147078 | A1 * | 6/2008 | Francis | A61B 19/46 606/102 |
| 2008/0147079 | A1 * | 6/2008 | Chin | A61B 17/1757 606/102 |
| 2008/0255575 | A1 * | 10/2008 | Justis | A61B 19/46 606/102 |
| 2009/0198240 | A1 * | 8/2009 | Kaufman | A61B 17/025 606/90 |
| 2010/0036443 | A1 * | 2/2010 | Hutton | A61B 17/7032 606/86 R |
| 2010/0114179 | A1 | 5/2010 | Moore et al. | |
| 2012/0035611 | A1 * | 2/2012 | Kave | A61B 19/46 606/102 |

OTHER PUBLICATIONS

European Search Report for PCT/US2012/033646 the counterpart application mailed on Jul. 21, 2014.

* cited by examiner

*Primary Examiner* — Zade Coley

(57) ABSTRACT

Apparatus and methods for measuring spacing between first and second bone screws engaged with first and second bone structures are provided. An apparatus comprises first and second arms operably engaged with a single pivot pin. The first arm includes a distal end adapted to engage the first bone screw, and a proximal end comprising a graduated scale. The second arm, operably engaged with the first arm via the single pivot pin, includes a distal end adapted to engage the second bone screw, and a proximal end comprising an indicator segment slidably engaged with the graduated scale. A position of the indicator segment relative to the graduated scale is therefore indicative of a spacing between the first and second bone screws.

20 Claims, 5 Drawing Sheets

APPARATUS AND METHOD FOR SIZING A CONNECTING ELEMENT FOR POSITIONING ALONG A BONE STRUCTURE

BACKGROUND

Various devices and methods for stabilizing bone structures have been used for many years. For example, the fracture of an elongated bone, such as a femur or humerus, can be stabilized by securing a plate to the fractured bone across the fracture. The plate extends across the fractured area and thus stabilizes the fractured components of the bones relative to one another in a desired position. When the fracture heals, the plate can be removed or left in place, depending on the type of plate that is used.

Another type of stabilization technique uses one or more elongated rods extending between components of a bone structure and secured to the bone structure to stabilize the components relative to one another. The components of the bone structure are exposed and one or more bone engaging fasteners are placed into each component. The elongated rod is then secured to the bone engaging fasteners in order to stabilize the components of the bone structure.

One problem associated with the above described stabilization structures is that the skin and tissue surrounding the surgical site must be cut, removed, and/or repositioned in order for the surgeon to access the location where the stabilization device is to be installed. This prepositioning of tissue causes trauma, damage, and scarring to the tissue. There are also risks that the tissue will become infected and that a long recovery time will be required after surgery for the tissue to heal.

Minimally invasive surgical techniques are particularly desirable in, for example, spinal and neurosurgical applications because of the need for access to locations within the body and the potential trauma to vital intervening tissues. The development of percutaneous minimally invasive spinal procedures has yielded a major improvement in reducing trauma, recovery time and post-operative pain. The benefits of minimally invasive techniques have also found application in surgeries for other locations in the body where it is desirable to minimize tissue disruption.

One potential disadvantage associated with minimally invasive techniques is that the tissue can obstruct access and visualization of the implantation location for an implant in the body of the patient. Accordingly, the optimally sized implant for implantation between anchors or other structures in the patient may not be readily determinable. While minimally invasive techniques have yielded benefits, there remains a need for instruments and methods that facilitate application of minimally invasive procedures during surgery.

SUMMARY

Apparatus and methods for measuring spacing between first and second bone screws engaged with first and second bone structures are provided. According to one aspect, an apparatus comprises a first arm having a distal end adapted to engage a first bone screw, and a proximal end comprising a graduated scale. A single pivot pin is operably engaged with the first arm between the distal end and the proximal end thereof. The apparatus also comprises a second arm operably engaged with the first arm via the single pivot pin. As described herein, the second arm has a distal end adapted to engage the second bone screw, and a proximal end comprising an indicator segment slidably engaged with the graduated scale. Therefore, a position of the indicator segment relative to the graduated scale may be indicative of a spacing between the first and second bone screws.

According to another aspect, a system for percutaneous implantation of spinal instrumentation is provided, the system comprising a first bone screw extender adapted to implant a first bone screw at a first bone structure and a second bone screw extender adapted to implant a second bone screw at a second bone structure. A caliper is also provided for measuring spacing between first and second bone screws engaged with first and second bone structures, wherein the caliper comprises a first arm having a distal end adapted to engage the first bone screw extender, and a proximal end comprising a graduated scale extending therefrom. The caliper also comprises a single pivot pin operably engaged with the first arm between the distal end and the proximal end thereof, and a second arm operably engaged with the first arm via the single pivot pin, the second arm having a distal end adapted to engage the second bone screw extender, and a proximal end comprising an indicator segment slidably engaged with the graduated scale of the first arm. A position of the indicator segment relative to the graduated scale may therefore be indicative of the spacing between the first and second bone screws, allowing a surgeon to accurately determine a length of spinal rod to be inserted to connect the first and second bone screws.

According to another aspect, a method is provided for measuring spacing between first and second bone screws engaged with first and second bone structures. In one aspect, the method comprises engaging a first bone screw extender with the first bone screw, engaging a second bone screw extender with the second bone screw, and pivoting a first arm and a second arm of a caliper relative to one another about a single pivot pin operably engaged with the first and second arms, such that the first and second arms of the caliper are insertable into the first and second bone screw extenders. The method further comprises inserting the first arm of the caliper into the first bone screw extender, wherein the first arm has a distal end configured to engage the first bone screw extender, and a proximal end comprising a graduated scale extending therefrom. The method further comprises inserting the second arm of the caliper in the second bone screw extender, wherein the second arm has a distal end configured to engage the second bone screw extender, and a proximal end comprising an indicator segment slidably engaged with the graduated scale of the first arm. Therefore, a position of the indicator segment relative to the graduated scale may be indicative of a spacing between the first and second bone screws.

Related features, aspects, embodiments, objects and advantages of the disclosed apparatuses and methods will be apparent from the following description.

DESCRIPTION OF THE ILLUSTRATED EMBODIMENTS

Figure 1:
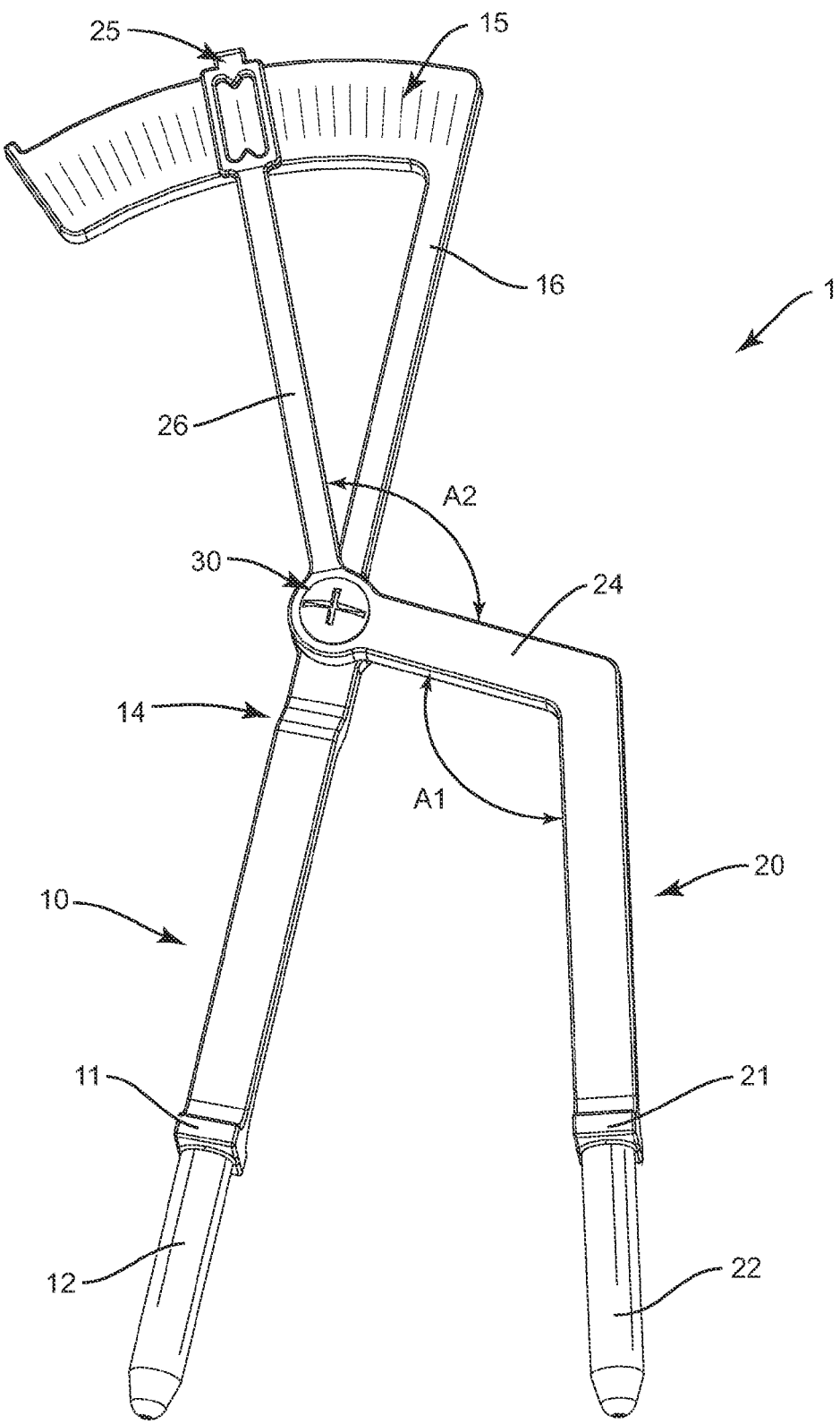
FIG. 1 is a perspective view of an apparatus for measuring spacing between first and second bone screws engaged with first and second bone structures, according to one embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Figure 3:
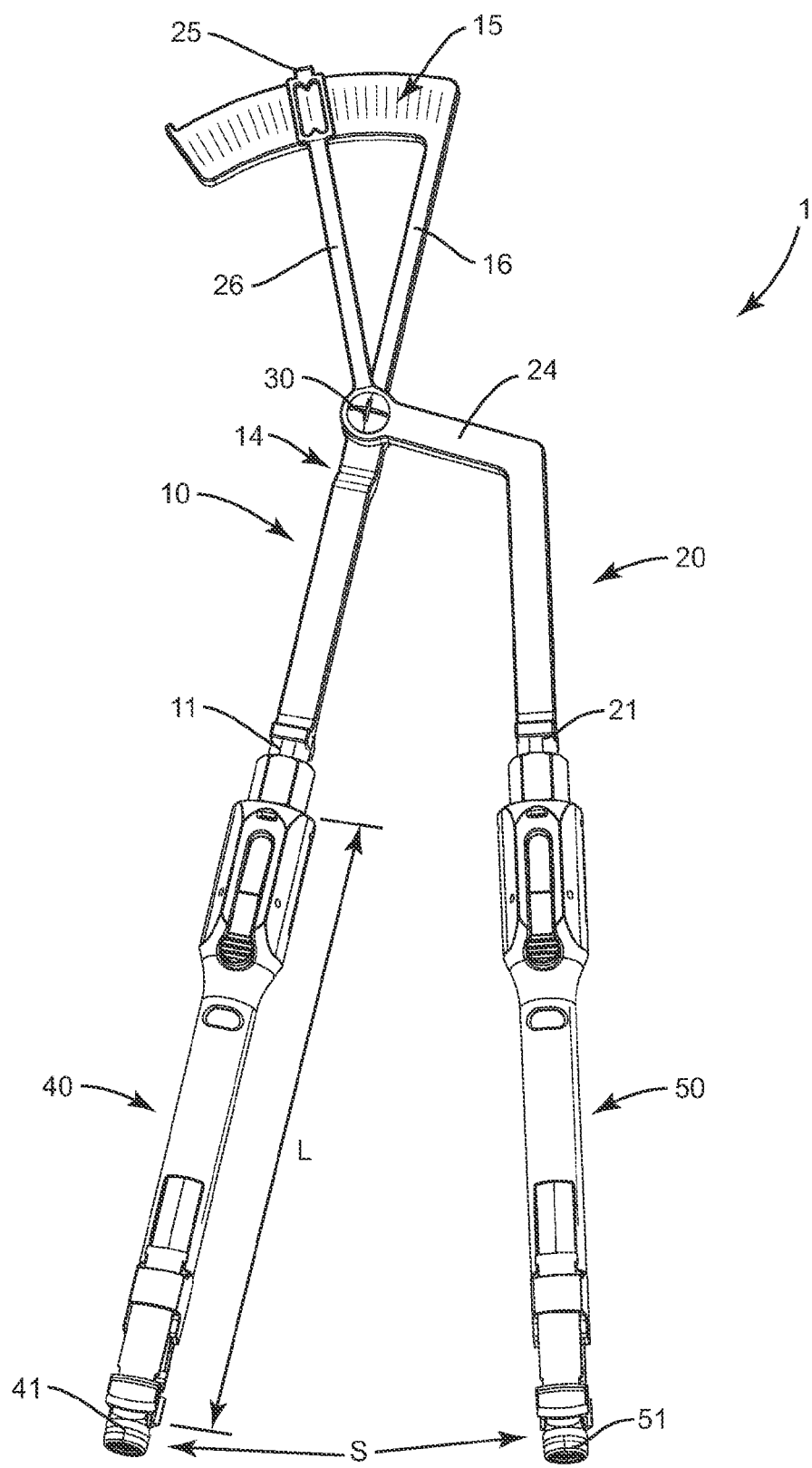
FIG. 3 is a perspective view of the apparatus of FIG. 1 engaged with first and second bone screw extenders.
Figure 5:
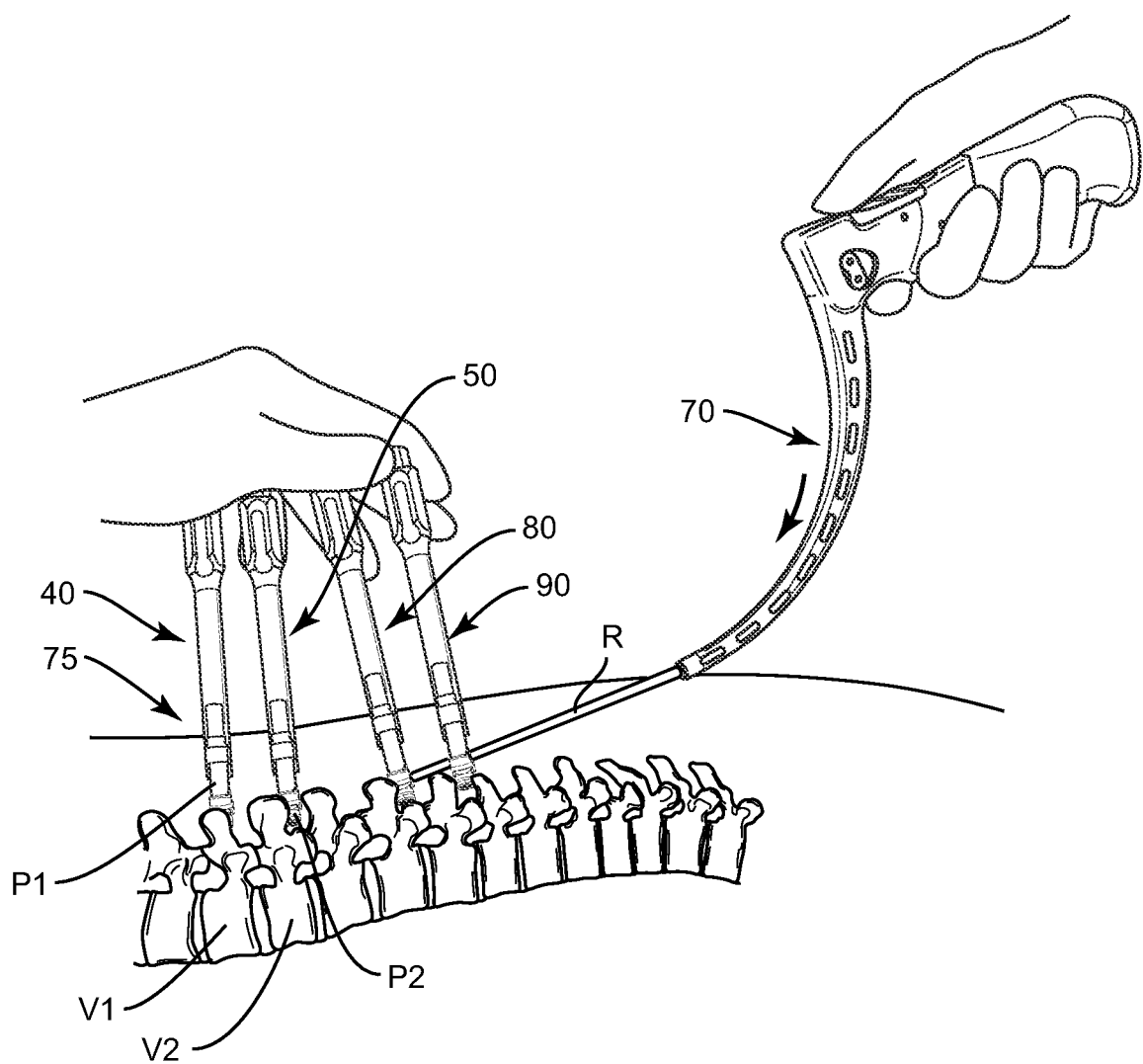
FIG. 5 is a perspective view of bone screws and associated screw extenders engaged with first and second bone structures as part of a percutaneous fixation procedure, and a percutaneous rod inserter device suitable for engaging a spinal rod with the bone screws.

Referring generally to FIG. 5, apparatus and method is provided for measuring spacing between first and second bone screws P1, P2 engaged with first and second bone structures V1, V2. As shown in FIG. 3, an apparatus, such as a caliper 1, may be inserted into bone screw extenders 40, 50 that may be engaged with bone screws P1, P2 as part of a spinal surgery. As shown in FIG. 5, a surgeon may wish to accurately measure and/or estimate the spacing S between adjacent first and second bone screws P1, P2 in a spinal surgery such that a spinal rod R having an appropriate length may be chosen from a plurality of spinal rod R sizes to connect adjacent first and second bone screws P1, P2. For example, as shown in FIG. 5, a surgeon may seek to estimate the length of spinal rod R that should be implanted using a minimally-invasive rod insertion technique such as that offered by the CD Horizon® Longitude™ Multi-level Percutaneous Fixation System developed by Medtronic Spinal and Biologics, of Memphis Tenn. The various embodiments described herein provide exemplary caliper 1 apparatus and related methods for accurately measuring the spacing S between adjacent first and second bone screws P1, P2 engaged with bone screw extenders 40, 50 such that a surgeon may be better informed when selecting spinal rod R components when performing spinal procedures. In other embodiments, exemplary caliper 1 apparatus and related methods described herein may include a caliper 1 that is sized and/or calibrated to measure spacing S between adjacent bone screws P1, P2 without the use of intervening bone screw extenders 40, 50 (such as in "open" or non-percutaneous surgical procedures).

Figure 4:
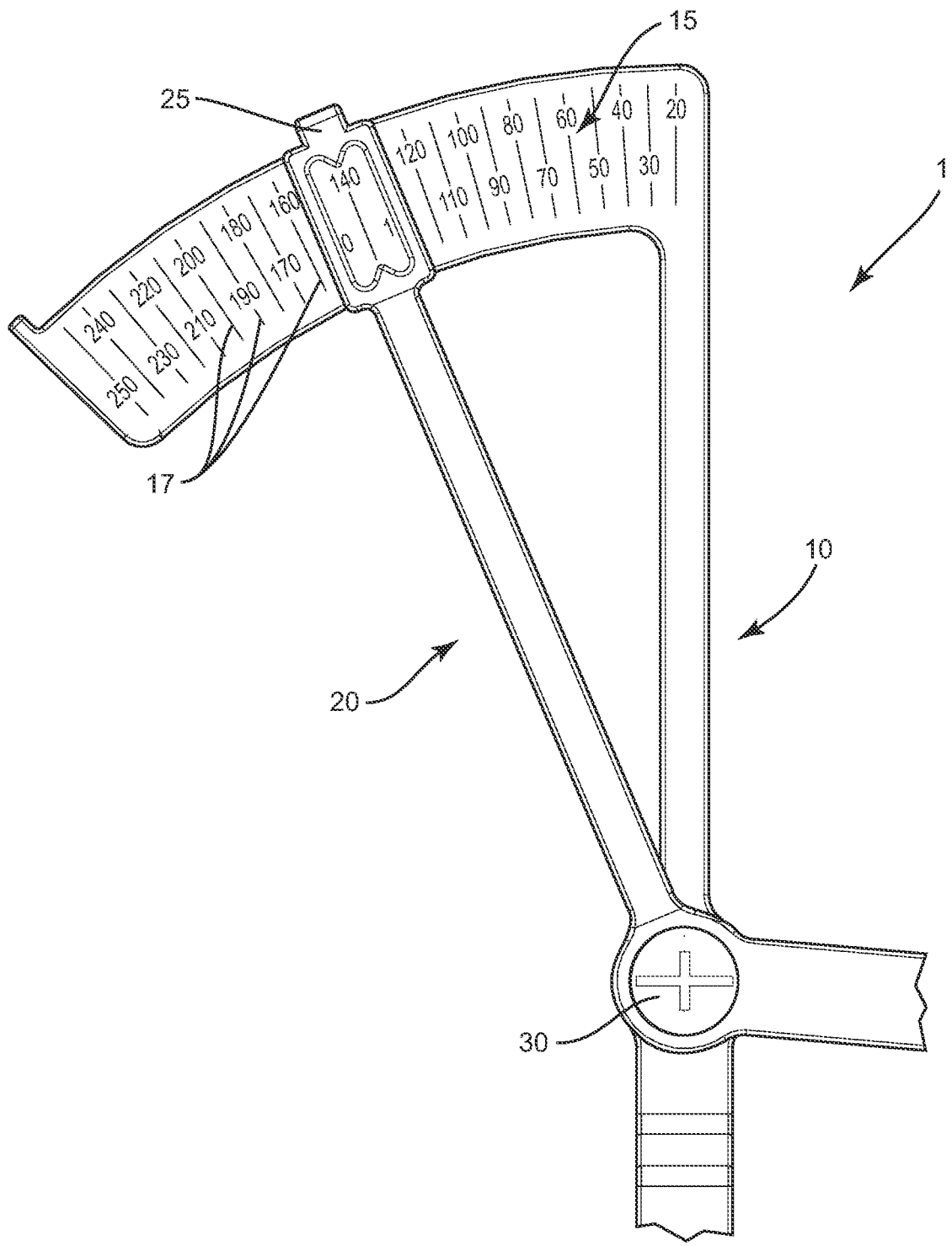
FIG. 4 is a perspective view of a proximal portion of an apparatus for measuring spacing between first and second bone screws engaged with first and second bone structures, according to one embodiment.

Referring to FIG. 1, in one embodiment, a caliper 1, may comprise a first arm 10 having a distal end 12 adapted to engage the first bone screw P1 (in some instances, via the bone screw extender 40, as shown in FIG. 4). The first arm 10 also comprises a proximal end 16 comprising a graduated scale 15 extending therefrom. The caliper 1 further comprises a single pivot pin 30 operably engaged with the first arm 10 between the distal end 12 and the proximal end 16 thereof. The caliper 1 further comprises a second arm 20 operably engaged with the first arm 10 via the single pivot pin 30. The second arm 20 also has a distal end 22 adapted to engage the second bone screw P2 (in some instances, via the bone screw extender 50, as shown in FIG. 4), and a proximal end 26 comprising an indicator segment 25 slidably engaged with the graduated scale 15 such that a position of the indicator segment 25 relative to the graduated scale 15 is indicative of a spacing S between the first and second bone screws P1, P2 (see FIG. 3, for example, where the spacing S is shown between distal ends 41, 51 of the bone screw extenders 40, 50, respectively).

Referring again to FIG. 1, the distal ends of the first and second arms 10, 20 may also comprise cylindrical elements 12, 22 configured to be insertable into a first bone screw extender 40 and a second bone screw extender 50 (see FIG. 3, for example) extending respectively from the first and second bone screws P1, P2 (see FIG. 5, for example). In some such embodiments, the distal ends of the first and second arms 10, 20 may also comprise stop elements 11, 21 formed thereon that may ensure that the cylindrical elements 12, 22 extend only a selected distance into a complementary set of cylindrical bores defined in the bone screw extenders 40, 50. In some embodiments, the extreme distal ends of the cylindrical elements 12, 22 may also be formed with a conical and/or tapered shape so as to ease the insertion of the cylindrical elements 12, 22 into the screw extenders 40, 50.

Figure 2:
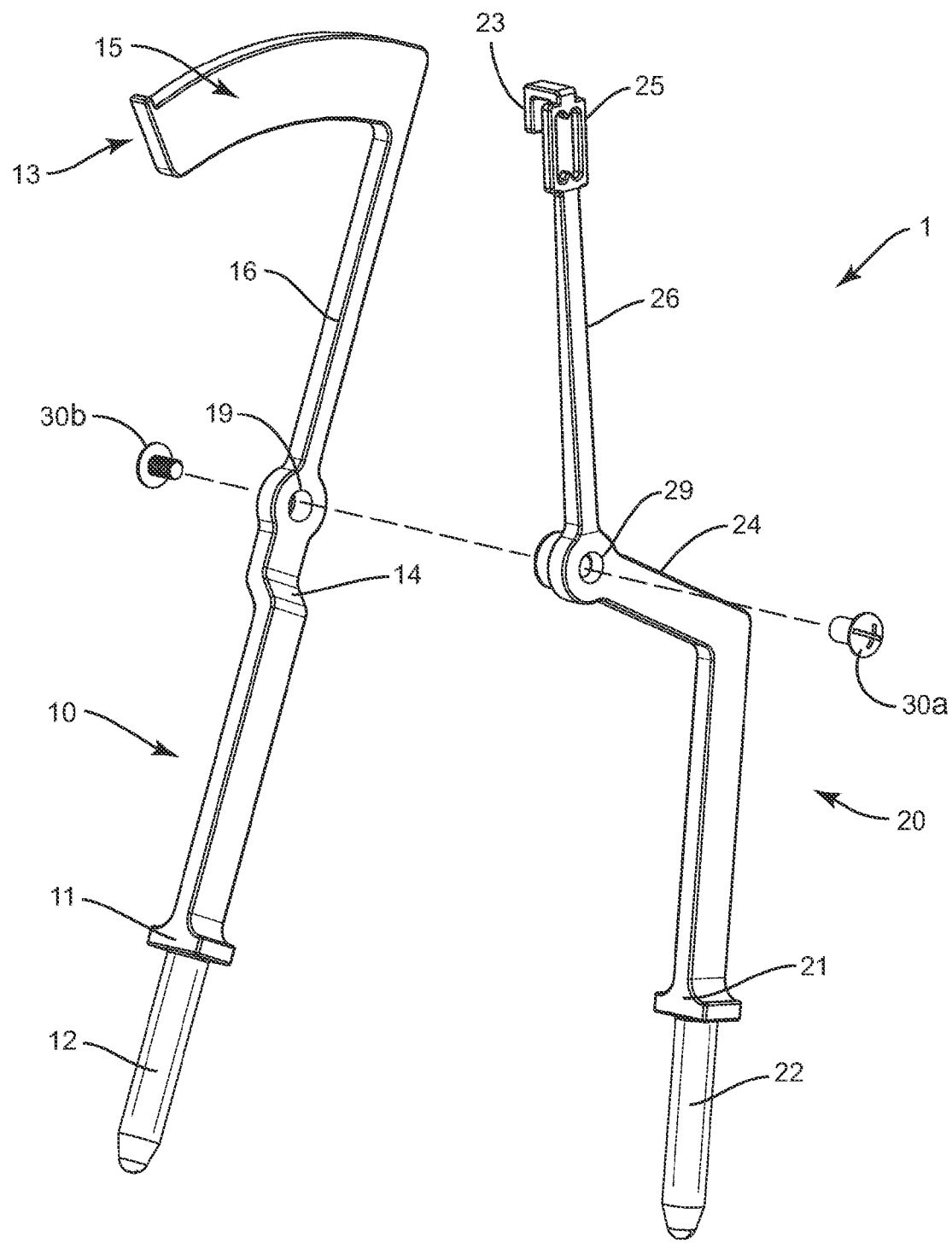
FIG. 2 is an exploded perspective view of the apparatus of FIG. 1.

Referring again to the first arm 10, shown generally in FIGS. 1-3, the distal and proximal ends 12, 16 of the first arm 10 may be assembled and/or formed to be substantially parallel. In some embodiments, the first arm 10 may be substantially straight along its length. In other embodiments, the first arm 10 may comprise an offset member 14 configured to place the distal end 12 of the caliper 1 in a common plane of movement with the corresponding distal end 22 of the second arm 20 of the caliper 1 such that each of the first and second arms 10, 20 may be engaged with a corresponding pair of bone screw extenders 40, 50 in a manner that yields a spacing S measurement that is accurately readable on the graduated scale 15 of the caliper 1.

As shown in FIG. 1, the graduated scale 15 may comprise an arcuate member extending from the proximal end 16 of the first arm 10. Furthermore, the second arm 20 may comprise a proximal end 26 comprising an indicator segment 25 slidably engaged with the graduated scale 15 such that a position of the indicator segment 25 relative to the graduated scale 15 is indicative of a spacing S between the first and second bone screws P1, P2. In some such embodiments, as shown generally in FIG. 4, the caliper 1 may comprise a plurality of markings 17 disposed on the graduated scale 15. In such embodiments, the plurality of markings 17 may be configured to account for a length of the first and second bone screw extenders 40, 50 such that a position of the indicator segment 25 relative to the graduated scale 15 is indicative of a screw spacing S between the first bone screw P1 and the second bone screw P2 operably engaged with distal ends 41, 51 of the first and second bone screw extenders 40, 50. For example, as shown in FIG. 4, the indicator segment 25 may define a window or other aperture through which the markings 17 of the graduated scale 15 may be visible to a surgeon, wherein the markings 17 are indicative of a length or other spacing S measurement between adjacent bone screws P1, P2 as indicated by the relative positions of the distal ends 12, 22 of the arms 10, 20 of the caliper 1. The markings 17 may be printed, etched, cut or otherwise made visible on the graduated scale and may be calibrated to adjust for variations in the geometry of the arms 10, 20, the position of the pivot pin 30 and/or whether or not bone screw extenders 40, 50 are present between the distal ends 12, 22 of the arms 10, 20 and the bone screws P1, P2. The surgeon may then select a spinal rod R (see FIG. 5, for example) having an appropriate length to connect adjacent bone screws P1, P2 implanted in bone structures V1, V2. The surgeon may implant the spinal rod R using a number of different available surgical techniques, including but not limited to those associated with the CD Horizon™ Longitude® system available from Medtronic Spinal and Biologics of Memphis, Tenn. as shown generally in FIG. 5.

As shown in FIGS. 1 and 2, the calipers 1 disclosed herein may be formed and/or constructed with a number of bends, angles and other geometric features that allow for the spacing S to be accurately reflected in the position of the indicator segment 25 relative to the graduated scale 15 when the distal ends 12, 22 of the caliper 1 are engaged with a first bone screw P1 and a second bone screw P2 (in some instances, with first and second bone screw extenders 40, 50 disposed therebetween). For example, as shown in FIG. 1, the second arm 20 of the caliper 1 may comprise a transverse member 24 disposed between the distal end 22 and the proximal end 26 of the second arm 20. It will be appreciated that the length and/or position of the transverse member 24 may be selected to account for differences in the length of the arms 10, 20, length of the bone screw extenders 40, 50 and/or other measurements associated with a particular surgical technique or spinal instrumentation that may be used with the caliper 1, such that the reading indicated by the position of the indicator segment 25 relative to the graduated scale 15 may accurately reflect the spacing S between adjacent bone screws P1, P2.

Other geometric features of the caliper 1 may also be selected to provide accurate measurements of the spacing S between adjacent bone screws P1, P2. For example, in some embodiments, the distal and proximal ends 22, 26 of the second arm 20 may be substantially parallel. Furthermore, the transverse member 24 may extend at a first obtuse angle A1 relative to the distal end 22 of the second arm 20. The transverse member 24 may also extend at a second obtuse angle A2 relative to the proximal end 26 of the second arm 20. In some embodiments, the first and second obtuse angles A1, A2 may be equal. Such geometric features may be utilized to accurately shape and size the caliper 1 components such that the graduated scale 15 (and the position of the indicator segment 25 relative to the graduated scale 15) accurately reflects a spacing S measured between the distal ends 12, 22 of the caliper 1. The described features of the caliper 1 may be adjusted and/or modified as will be appreciated by one of skill in the art to allow for the accommodation of varying bone screw extenders 40, 50 having lengths L (see FIG. 3).

Referring again to FIG. 3, some embodiments may comprise a complete system for percutaneous implantation of spinal instrumentation comprising a caliper 1, a caliper-compatible first bone screw extender 40 adapted to implant a first bone screw P1 at a first bone structure V1 and a caliper-compatible second bone screw extender 50 adapted to implant a second bone screw P2 at a second bone structure V2 (see also, FIG. 5 showing the extenders 40, 50 and bone screws P1, P2 placed relative to bone structures V1, V2. Such system embodiments may also comprise a caliper 1 as described herein having suitable geometric configuration for measuring spacing S between adjacent bone screws P1, P2 engaged with distal ends 41, 51 of the extenders 40, 50 provided as part of the system (see FIG. 3). As depicted generally in FIG. 3, the caliper 1 may comprise a first arm 10 having a distal end 12 adapted to engage the first bone screw extender 40, and a proximal end 16 comprising a graduated scale 15 extending therefrom. The caliper 1 may also comprise a single pivot pin 30 operably engaged with the first arm 10 between the distal end 12 and the proximal end 16 thereof, and a second arm 20 operably engaged with the first arm 10 via the single pivot pin 30. The second arm 20 comprises a distal end 22 adapted to engage the second bone screw extender 50 and a proximal end 26 comprising an indicator segment 25 slidably engaged with the graduated scale 15 such that a position of the indicator segment 25 relative to the graduated scale 15 (and/or relative to markings 17 thereon, as shown in FIG. 4) is indicative of a spacing S between the first and second bone screws P1, P2. As shown in FIG. 5, once the spacing S is determined using the caliper 1, a surgeon may also use a rod introducer device 70 configured for operably engaging a spinal rod R between the first and second bone screws P1, P2, wherein a length of the spinal rod R is determined at least in part by the spacing S indicated by the graduated scale 15 of the caliper 1.

Various methods are also provided for measuring spacing S between first and second bone screws P1, P2 engaged with first and second bone structures V1, V2. In one embodiment, such a method comprises engaging a first bone screw extender 40 with the first bone screw P1, engaging a second bone screw extender 50 with the second bone screw. Engaging the first bone screw P1 and the first bone screw extender 40 with the first bone structure, and engaging the second bone screw P2 and the second bone screw extender 50 with the second bone structure V2 (see FIG. 5). Such method embodiments further comprise pivoting a first arm 10 and a second arm 20 of a caliper 1 (see FIG. 1) relative to one another about a single pivot pin 30 operably engaged with the first and second arms 10, 20, such that the first and second arms 10, 20 of the caliper 1 are insertable into the first and second bone screw extenders 40, 50, respectively.

The method further comprises inserting the first arm 10 of the caliper 1 into the first bone screw extender 40, wherein the first arm 10 has a distal end 12 configured to engage the first bone screw extender 40. For example, in some embodiments, the distal end 12 comprises a cylindrical element configured to fit within a complementary cylindrical channel defined in the bone screw extenders 40, 50. As described herein, the first arm 10 also includes a proximal end 16 comprising a graduated scale 15 extending therefrom. The method further comprises inserting the second arm 20 of the caliper 1 in the second bone screw extender 50. As described herein, the second arm 20 may be provided with a distal end 12 (which may comprise a cylindrical element as shown in FIGS. 1 and 2) configured to engage the second bone screw extender 50, and a proximal end 26 comprising an indicator segment 25 slidably engaged with the graduated scale 15 of the first arm 10 such that a position of the indicator segment 25 relative to the graduated scale 15 is indicative of a spacing S between the first and second bone screws P1, P2 (see FIG. 5, for reference).

Various method embodiments may further comprise removing the first and second arms 10, 20 of the caliper 1 from the first and second bone screw extenders 40, 50 and selecting a spinal rod R having a length compatible with the indicated spacing S between the first and second bone screws P1, P2 (see FIG. 5, for example). The measurement of the spacing S is then employed to select a connecting element (such as a spinal rod R) of the desired length, or used to modify the length of an existing spinal rod R or other connecting element, to fit the space S between bone screws P1, P2.

In some embodiments, the caliper 1 may be used multiple times in a single procedure to determine an overall length of spinal rod R (or other connector) that may be used to connect multi-level spinal instrumentation. For example, the caliper 1 may be used to determine an overall length of spinal rod R to connect a series of four bone screws (attached to four bone screw extenders as shown generally in FIG. 5) by: first measuring the spacing S between the first and second bone screw extenders 40, 50; then measuring the spacing S between the second and third bone screw extenders 50, 80; then measuring the spacing S between the third and fourth bone screw extenders 80, 90; and finally adding the three spacing S measurements to determine an overall linear length of spinal rod R to connect the instrumentation.

As shown generally in FIG. 5, the method may also comprise connecting the first and second bone screws P1, P2 using the spinal rod R by operably engaging the spinal rod R with a head portion of the first and second bone screws P1, P2. This step may be accomplished, for example, using a rod-introduction device 70 as shown generally in FIG. 5. In spinal surgical procedures, the selected connecting element (such as a spinal rod R) can be delivered to one or more vertebrae V1, V2 in an anterior approach, a posterior approach, a lateral approach, postero-lateral approach, a transforaminal approach, or an anterior-oblique approach, for example. Vertebrae V1, V2 can comprise all or a portion of the cervical, thoracic, lumbar and sacral vertebrae of the spinal column. In addition to stabilization of one or more spinal motion segments with spinal rod R, other spinal repair procedures can be performed as an additional procedure, including procedures to fuse vertebrae with one or more implants or bone graft, to replace one or more vertebral bodies, to repair annulus tissue, or to insert artificial disc components, for example. Applications in non-spinal procedures are also contemplated.

The spinal rod R is rigid in one embodiment to prevent motion between the bone structures V1, V2 to which it is attached via the bone screws P1, P2. In another embodiment spinal rod R is fabricated from one or more components that are flexible or exhibit at least some flexibility or non-rigidity to permit motion of the stabilized vertebral level or levels. Some examples include extruded components, machined components, molded components, formed components, and milled components.

The various embodiments described herein may also be used to measure spacing S for a number of different types of connecting element that may include any one or more of sheets, tethers, cords, planar members, bands, wires, cables, rods, bars, woven structures, or any other component capable of forming or being formed into the implant body. In a further form, such connecting element is resilient and/or elastic in whole or in part so it can assume various shapes during and after insertion and attachment while exhibiting a tendency to return to its natural form. In yet another form, connecting element is substantially inelastic so that the shape achieved upon insertion or deformation is maintained.

Connecting element and/or spinal rod R can be made from any biocompatible material, material of synthetic or natural origin, and material of a resorbable or non-resorbable nature. Suitable examples of implant material include autograft, allograft or xenograft; tissue materials including soft tissues, connective tissues, demineralized bone matrix and combinations thereof; resorbable materials including polylactide, polyglycolide, tyrosinederived polycarbonate, polyanhydride, polyorthoester, polyphosphazene, calcium phosphate, hydroxyapatite, bioactive glass, collagen, albumin, fibrinogen and combinations thereof; and non-resorbable materials including polyethylene, polyester, polyvinyl alcohol, polyacrylonitrile, polyamide, polytetrafluoroethylene, polyparaphenylene terephthalamide, cellulose, carbon-reinforced polymer composites, PEEK, shape memory alloys, titanium, titanium alloys, cobalt chrome alloys, stainless steel, and combinations thereof.

One specific example of a suitable bone screw P1, P2 usable in the various embodiments described herein is a multi-axial screw such as described in U.S. Pat. Nos. 5,797, 911 and 5,879,350, each of which is incorporated herein by reference. Other examples for bone screws P1, P2 include uni-axial screws, bolts, specialty pedicle screws, and pins, for example. It is further contemplated that one or more of the bone screws P1, P2 can include a multi-axial head and one or more of the other anchors include a uni-axial head. The bone screws P1, P2 can be cannulated to facilitate placement over a guidewire and into the vertebra in minimally invasive procedures, or can be non-cannulated. Cannulated bone screws P1, P2 can further include one or more fenestrations or openings for placement of bone cement or other material therethrough.

Pre-operative planning and image guided navigation of anchor placement and installation of the connecting element and/or spinal rod R are also contemplated. The surgical techniques can employ any type of known imaging system to determine and locate optimum placement and orientation of the anchors in the bony structure and, if necessary, to locate skin locations for percutaneous puncture entry of the anchors and connecting element.

Bone screw P1, P2 insertion can be monitored using any known viewing instrument or apparatus, and performed under any known surgical technique. For example, bone screws P1, P2 can be placed through a cannula or sleeve inserted through the skin that forms a working channel to a location over the target bone structures V1, V2. Bone screw placement into the bone structure can be monitored endoscopically, microscopically, fluoroscopically, radiographically and/or with naked eye visualization through the cannula. Bone screw placement can also be performed through micro-incisions, or through open incisions in which the skin and tissue is retracted to expose the bony structure.

In one specific technique for placing bone screws P1, P2, a guidewire of sufficient length is inserted percutaneously and anchored to the bony structure, such as a pedicle of the vertebra (V1, V2, for example). The guidewire is coupled to a trackable instrument that is tracked via an image guided surgical system that generates a display on a computer monitor. With the guidewire secured at the appropriate location on the bone structure, various instruments for preparing and inserting the bone screw into the bone structure can be guided by the guidewire. The preparation and insertion can be monitored via a tracking instrument coupled to the various preparation and insertion instruments, and anchor extensions (such as bone screw extenders 40, 50) are mounted to the engaged bone screw P1, P2. The length of the connecting element (such as spinal rod R) between the engaged bone screws P1, P2 is then determined with caliper 1 mounted to the proximal ends of the bone screw extenders 40, 50 and manipulated as discussed herein.

Bone screws P1, P2 can be engaged on both sides of a midline of the spine, and along one or more levels of the spine. The bone screws P1, P2 can be engaged to stabilize adjacent vertebra in conjunction with any minimally invasive or open surgical techniques for placement of one or more implants into a disc space. For example, one or more interbody fusion devices or intervertebral spacers may be inserted into the disc space via an anterior, anterior oblique, lateral, postero-lateral, or transforaminal approach, and a connecting element (including, but not limited to spinal rod R) can be positioned and engaged to the spinal column segment from a posterior approach (see FIG. 5, for example). Further, connecting element (such as spinal rod R) can be used to stabilize adjacent vertebrae, or any other bony structure, without placement of implants between structures comprising bony segment.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. An apparatus for measuring spacing between first and second bone screws engaged with first and second bone structures, comprising:
a first arm having a distal end and a proximal end comprising a graduated scale extending therefrom;
a single pivot pin operably engaged with the first arm between the distal end and the proximal end thereof, wherein a proximal portion of the first arm defines a first longitudinal axis and a distal portion of the first arm on the opposite side of the single pivot pin defines a second longitudinal axis that is offset from the first longitudinal axis; and
a second arm operably engaged with the first arm via the single pivot pin, the second arm having a distal end defining a third longitudinal axis and a proximal end defining a fourth longitudinal axis that intersects the single pivot pin, the proximal end comprising an indicator segment slidably engaged with the graduated scale such that a position of the indicator segment relative to the graduated scale is indicative of a spacing between the first and second bone screws, the distal portion being movable relative to the second arm in a first plane and the proximal portion being movable relative to the second arm in a second plane that is offset from the first plane, the proximal and distal ends of the second arm being movable relative to the first arm in the first plane,
wherein the first arm comprises a first cylindrical element that extends along the second longitudinal axis and the distal end of the second arm comprises a second cylindrical element that extends along the third longitudinal axis.

2. The apparatus of claim 1, wherein the entire second arm between the distal and proximal ends is substantially linear.

3. The apparatus of claim 1, wherein the graduated scale comprises an arcuate member extending from the proximal end of the first arm.

4. The apparatus of claim 1, wherein the second arm comprises a transverse member disposed between the distal and proximal ends thereof.

5. The apparatus of claim 4, wherein the distal and proximal ends of the second arm are substantially parallel and wherein the transverse member extends at a first obtuse angle relative to the distal end of the second arm and at a second obtuse angle relative to the proximal end of the second arm.

6. The apparatus of claim 5, wherein the first and second obtuse angles are equal.

7. The apparatus of claim 1, wherein the distal ends of the first and second arms rotate about one another in the first plane.

8. The apparatus of claim 1, further comprising a plurality of markings disposed on the graduated scale, the plurality of markings being configured to account for a length of first and second bone screw extenders that are coupled to the bone screws such that a position of the indicator segment relative to the graduated scale is indicative of a screw spacing between the first bone screw and the second bone.

9. The apparatus of claim 1, wherein:
at least one of the first and second cylindrical elements is tapered; and
the indicator segment comprises a window configured for viewing a portion of the graduated scale indicative of the spacing between the first and second bone screws.

10. The apparatus of claim 1, wherein the portions of the first arm on either side of the single pivot pin are linear.

11. The apparatus of claim 1, wherein the first cylindrical element is free of any projections that extend transverse to the second longitudinal axis and the second cylindrical element is free of any projections that extend transverse to the third longitudinal axis.

12. The apparatus of claim 1, wherein the cylindrical elements each including a body having a uniform diameter and a tapered tip that extends from the body.

13. The apparatus of claim 12, wherein the tapered tips are extreme distal ends of the cylindrical elements.

14. The apparatus of claim 12, wherein the first arm comprises a first stop element comprising a flange that extends transverse to the second longitudinal axis, the body of the first cylindrical element being positioned between the tapered tip of the first cylindrical element and the first stop element.

15. The apparatus of claim 12, wherein the body and the tapered tip of the first cylindrical element are coaxial with the second longitudinal axis and the body and the tapered tip of the second cylindrical element are coaxial with the third longitudinal axis.

16. An apparatus for measuring spacing between first and second bone screws engaged with first and second bone structures, comprising:
a first arm having a distal end and a proximal end comprising a graduated scale extending therefrom;
a single pivot pin operably engaged with the first arm between the distal end and the proximal end thereof, wherein a proximal portion of the first arm defines a first longitudinal axis and a distal portion of the first arm on the opposite side of the single pivot pin defines a second longitudinal axis that is offset from the first longitudinal axis; and
a second arm operably engaged with the first arm via the single pivot pin, the second arm having a distal end defining a third longitudinal axis and a proximal end defining a fourth longitudinal axis that intersects the single pivot pin, the proximal end comprising an indicator segment slidably engaged with the graduated scale such that a position of the indicator segment relative to the graduated scale is indicative of a spacing between the first and second bone screws, the distal portion being movable relative to the second arm in a first plane and the proximal portion being movable relative to the second arm in a second plane that is offset from the first plane, the proximal and distal ends of the second arm being movable relative to the first arm in the first plane,
wherein at least one of the first arm and the second arm comprises a cylindrical element.

17. The apparatus of claim 16, wherein the cylindrical element is free of any projections.

18. The apparatus of claim 16, wherein the second arm comprises a transverse member disposed between the distal and proximal ends thereof, the distal and proximal ends of the second arm being substantially parallel, the transverse member extending at a first obtuse angle relative to the distal end of the second arm and at a second obtuse angle relative to the proximal end of the second arm that is equal to the first obtuse angle.

19. An apparatus for measuring spacing between first and second bone screws engaged with first and second bone structures, comprising:
a first arm having a distal end and a proximal end comprising a graduated scale extending therefrom;
a single pivot pin operably engaged with the first arm between the distal end and the proximal end thereof, wherein a proximal portion of the first arm defines a first longitudinal axis and a distal portion of the first arm on the opposite side of the single pivot pin defines a second longitudinal axis that is offset from the first longitudinal axis; and a second arm operably engaged with the first arm via the single pivot pin, the second arm having a distal end defining a third longitudinal axis and a proximal end defining a fourth longitudinal axis that intersects the single pivot pin, the proximal end comprising an indicator segment slidably engaged with the graduated scale such that a position of the indicator segment relative to the graduated scale is indicative of a spacing between the first and second bone screw, the distal portion being movable in a first plane and the proximal portion being movable in a second plane that is offset from the first plane, the proximal and distal ends of the second arm being movable relative to the first arm in the first plane.

20. The apparatus of claim 19, wherein the second arm comprises a transverse member disposed between the distal and proximal ends thereof, the distal and proximal ends of the second arm being substantially parallel, the transverse member extending at a first obtuse angle relative to the distal end of the second arm and at a second obtuse angle relative to the proximal end of the second arm that is equal to the first obtuse angle.

* * * * *